United States Patent

Hösel et al.

Patent Number: 6,136,545
Date of Patent: *Oct. 24, 2000

[54] HOMOGENEOUS DETECTION METHODS FOR THE DETERMINATION OF SUBPOPULATIONS OF AN ANALYTE

[75] Inventors: Wolfgang Hösel, Tutzing; Wolfgang Mutter, Bernried, both of Germany

[73] Assignee: Roche Diagnostics GmbH, Mannheim, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/926,452

[22] Filed: Sep. 10, 1997

[30] Foreign Application Priority Data

Sep. 13, 1996 [DE] Germany .......................... 196 37 418

[51] Int. Cl.⁷ ...................... G01N 33/536; G01N 33/546; G01N 33/554
[52] U.S. Cl. ........................ 435/7.1; 435/7.8; 436/519; 436/524; 436/533
[58] Field of Search .................. 435/7.1, 7.2, 7.8; 436/519, 524, 533

[56] References Cited

U.S. PATENT DOCUMENTS 4,829,011  5/1989  Gibbons ................. 436/512

FOREIGN PATENT DOCUMENTS

| 0 074 520 | 3/1983 | European Pat. Off. . |
| 0 166 623 | 1/1986 | European Pat. Off. . |
| 0 260 079 | 3/1988 | European Pat. Off. . |
| 0 323 909 | 7/1989 | European Pat. Off. . |
| 0 337 410 | 10/1989 | European Pat. Off. . |
| 0 516 529 | 12/1992 | European Pat. Off. . |
| 43 09 393 A1 | 9/1994 | Germany . |

OTHER PUBLICATIONS

Database WPI on Dialog, Derwent Info. Ltd., No. 010028179 and 00635482, English abstract, EPA 617285, A and A2, Sep. 28, 1994.
International Publication No. WO 84/04396, published Nov. 8, 1984.

*Primary Examiner*—Donna C. Wortman
*Assistant Examiner*—Brenda G. Brumback
*Attorney, Agent, or Firm*—Arent Fox Kintner Plotkin Kahn

[57] ABSTRACT

The invention concerns a method for the determination of an analyte in a sample liquid wherein the sample liquid is incubated with (a) a first receptor which binds to a first epitope that is only present once on the analyte and is immobilized on a particulate carrier material and (b) a second receptor which binds to a second epitope on the analyte and has at least two binding sites for the second epitope, the first epitope being different from the second epitope and the analyte is determined by means of the binding to both receptors.

15 Claims, 1 Drawing Sheet

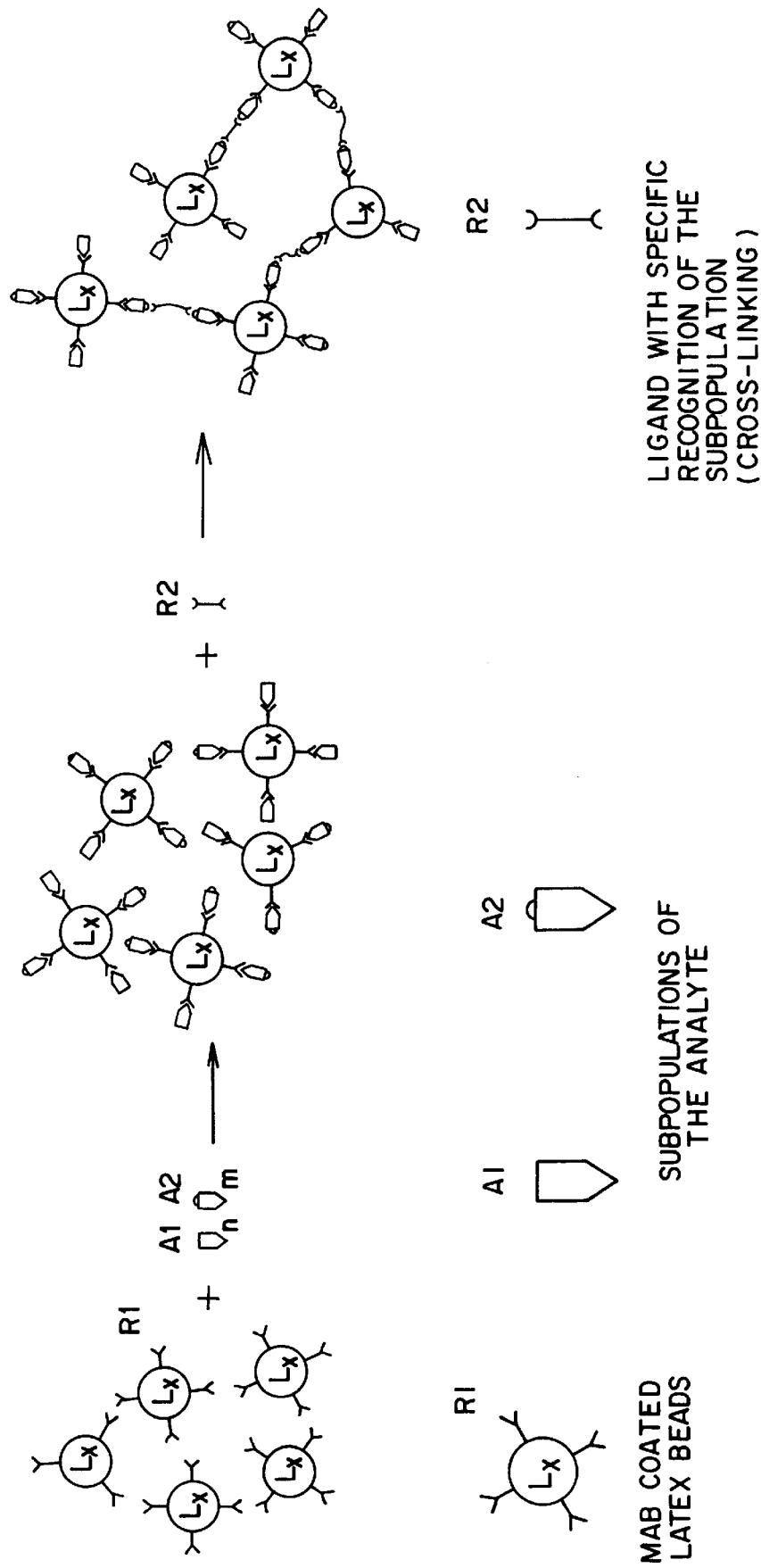

HOMOGENEOUS DETECTION METHODS FOR THE DETERMINATION OF SUBPOPULATIONS OF AN ANALYTE

DESCRIPTION

The present invention concerns a method for the determination of an analyte in a sample liquid by binding to a first receptor capable of specific binding to the analyte which is immobilized on a particulate carrier material present in the sample liquid and by agglutination with a second analyte-specific receptor, as well as a new reagent combination for carrying out such a method. This method is especially suitable for the qualitative or/and quantitative determination of subpopulations of an analyte.

Immunological detection methods based on the agglutination principle have been known for a long time. In these methods an analyte to be determined is mixed with a receptor or binding partner directed against the analyte under conditions in which an agglutination of the reaction partners takes place. The agglutination caused by the immunological reaction leads to particle aggregates whose light scattering properties differ from those of the starting substances which enables the analyte concentration to be determined.

The use of several receptors directed against the analyte to be determined in an immunological detection method is also known. Thus DE-OS 36 33 497 describes an immunometric determination method for an antigenic substance having at least two antibody binding sites in which a liquid sample containing this substance is incubated sequentially or in one step with an immobilized, unlabelled first specific antibody and a second specific labelled antibody to form a detectable solid phase-bound ternary complex of the substance to be determined and the two antibodies. The antigen concentration is determined over the entire measuring range in a first measurement and afterwards the sample is subjected to a second measurement.

Sandwich and nephelometric immunological tests are described in U.S. Pat. No. 4,595,661 which, in order to reduce the Hook effect, additionally contain at least one further antibody which has a lower affinity for the analyte in addition to the highly specific antibodies that are normally present in an immunological test.

EP-A-0 572 845 discloses a method for the immunochemical determination of an analyte in a sample by means of a first immobilized specific binding partner and a second specific binding partner which directly or indirectly carries a label wherein a binding factor is additionally added which has more than one bindable site for the analyte to be detected and has no affinity for the immobilized specific binding partner and which is not labelled.

DE-OS 43 09 393.0 discloses a method for the determination of an analyte by using a first analyte-specific receptor which is immobilized on a particulate carrier material and a second soluble analyte-specific receptor which has at least two binding sites for the analyte.

The Japanese unexamined laid-open patent applications 4-344465, 1-301165 and 59-92353 also disclosed the use of several analyte-specific receptors in an immunological detection method.

None of the methods described above is, however, suitable as a homogeneous detection method for the determination of subpopulations of an analyte e.g. for the quantitative determination of the presence of particular carbohydrate structures in glycoproteins. The known homogeneous immunoassays each only serve to determine the total amount of an analyte; subpopulations of the analyte which may have to be determined are isolated in a sample preparation step and thereafter determined in the actual test. However, such methods are time-consuming and moreover can lead to errors e.g. due to losses during the isolation of the subpopulations to be determined. In order to avoid these disadvantages heterogeneous immunoassays have up to now had to be carried out with bound/free separations which, however, in turn are considerably more complicated than homogeneous immunoassays.

The objective of the present invention was to provide a new method for the determination of subpopulations of an analyte in which the disadvantages of the state of the art are at least partially eliminated.

This objective is achieved by a method for the determination of an analyte in a sample liquid which is characterized in that the sample liquid is incubated with (a) a first receptor which binds to a first epitope which is only present once on the analyte and is immobilized on a particulate carrier material and (b) a second receptor which binds to a second epitope on the analyte and has at least two binding sites for the second epitope, the first epitope being different from the second epitope, and the analyte is determined by means of the binding to both receptors.

The invention is based on the concept that a first receptor, which is directed against an epitope which is only present once on the analyte to be determined e.g. a macromolecule, is bound to the surface of a particulate carrier material. When the immobilized first receptor is added to the analyte it binds to the particulate carrier material. However, no cross-linking takes place since the epitope recognized by the first receptor is only present once on the analyte. When the second receptor is added which recognizes another specific structure on the analyte, which may also optionally be present several times, and which has at least two binding sites for this structure, the particles of the carrier material are cross-linked by this second receptor. If a second receptor is selected which recognizes a structure which is only present in one subpopulation of the analyte to be determined, cross-linking only takes place for that fraction of the analyte which possesses the structure that is to be specifically recognized. The extent and the rate of cross-linking depend on the concentration of this analyte subpopulation. The determination of these concentrations can for example be measured photometrically by the increase of the absorbance at a suitable wavelength. In this manner it is possible to very simply detect subpopulations of an analyte without the necessity of a bound/free separation or of an isolation step.

The order of addition of the reaction partners is not critical i.e. the sample can be firstly mixed with the first immobilized receptor and then the second receptor can be added, or both receptors can be added simultaneously to the sample.

In the method according to the invention two analyte-specific receptors are used which each recognize different epitopes i.e. surface structures on the analyte and preferably bind to these with high affinity. All substances capable of binding come into consideration for the method according to the invention which bind strongly enough to the analyte under the test conditions to enable a determination.

The first receptor is immobilized on a particulate carrier material. Examples of suitable particulate carrier materials are latex particles, inorganic materials such as metal, metal oxide or carbon particles, liposomes or cells such as bacterial cells. The immobilization of receptors on such carrier materials and the use of the resulting conjugates in agglutination tests is known from the state of the art. Latex particles are particularly preferred particulate carrier materials.

All substances capable of binding are suitable as the first receptor which can react with an epitope which is only present once on an analyte e.g. antibodies, fragments and derivatives thereof, lectins, aptamers and membrane receptors. Specific preferred examples of the first immobilized receptor are monoclonal antibodies, monospecific polyclonal antibodies or/and fragments of such antibodies. Such antibodies can for example be produced by using immunogens which contain a pre-determined structure that is only present once on the analyte surface such as a peptide sequence. Suitable antibodies are for example monoclonal antibodies against salivary amylase (U.S. Pat. No. 4,939, 082), creatine kinase MB (WO94/25617), follicle-stimulating hormone (EP-86 102 589.8), luteinizing hormone (U.S. Pat. No. 5,248,593) and human choriogonadotropin (Boehringer Mannheim, Cat. No. 1200 933). Further preferred examples of the first receptor are lectins which recognize a carbohydrate structure that is only present once on the analyte.

All substances capable of binding (see above) come into consideration as the second receptor which serves for the agglutination which have at least two binding sites for a second epitope that is present on the analyte, this epitope preferably only occurring on a fraction or subpopulation of the analyte. Substances which only have a single binding site such as single-chain antibodies, aptamers, membrane receptors, can be converted into suitable second receptors by dimerization or polymerization. Specific examples of second receptors are, among others, monoclonal antibodies which are directed against phosphotyrosine, phosphoserine and phosphothreonine for the determination of phosphorylated fractions of particular proteins; the lectin concanavalin A or monoclonal antibodies with an appropriate specificity for the determination of non-enzymatically glycated proteins such as serum albumin, hemoglobin; the lectins RCA 120 described in the application examples for the determination of asialo glycoproteins as well as SNA for the determination of sialylated glycoproteins. Numerous further lectins can be used analogously depending on their specificity to detect glycoproteins with different structures.

The second receptor is preferably in a soluble and non-immobilized form and is specific for a subpopulation of the analyte i.e. the second receptor recognizes only one particular form of the analyte which is immobilized on the particulate carrier material by its binding to the first receptor whereas other forms of the immobilized analyte are not recognized.

If an antibody and a lectin are used as the receptor combination, it may in some cases be useful to modify the carbohydrates present on the antibody to destroy their binding capacity for lectins. This can for example be achieved by oxidation with periodate and subsequent inactivation of the aldehyde groups that are formed during the oxidation by treatment with ethanolamine.

BRIEF DESCRIPTION OF THE DRAWING

A preferred embodiment of the method according to the invention is elucidated in more detail in FIG. 1 of the attached drawing.

In this method latex particles ($L_x$) coated with monoclonal antibodies R1 are mixed with a sample which contains the analyte to be determined. The analyte to be determined is present as a mixture of at least two subpopulations (A1 and A2) which are present in proportions n and m (100−n) % of the total amount of the analyte. Both subpopulations of the analyte bind to the latex particles. Cross-linking does not take place.

In the next reaction step a second soluble receptor R2 is added which is specific for the subpopulation A2 of the analyte. The addition of R2 leads to a cross-linking of the latex particles which results in a change in the optical properties of the measuring medium. The concentration of the subpopulation A2 of the analyte can be determined by means of the rate or/and the extent of this change.

The analyte is preferably determined by measuring the intensity of scattered light (nephelometry) or by measuring the loss of intensity of light passing through the medium (turbidimetry).

The concentration of the analyte to be determined or of the analyte subpopulation to be determined is proportional to the increase of the optical absorbance in the measuring medium. A calibration curve is preferably established to quantify the results obtained. For this samples are preferably measured which contain known amounts of the analyte to be determined or of the analyte subpopulation to be determined. The content of the analyte or of the analyte subpopulation in an unknown sample to be determined is read from the calibration curve after measuring the agglutination rate.

If the analyte to be determined is a protein, a second receptor can be used which is specific for a subpopulation of this protein that differs from other subpopulations of the protein by the presence or absence of a secondary modification. Such secondary modifications may for example be a glycosylation, a certain type of glycosylation e.g. the presence of a certain carbohydrate partial structure such as of a sialic acid residue, a phosphorylation or a sulfation.

One example of analyte subpopulations which can be determined by the method according to the invention are certain glycosylation forms of lipoproteins such as the asialo form of apolipoprotein B. In this case an antibody against the lipoprotein can for example be used as the first receptor which is specific for a surface structure which only occurs once and, as the second receptor, a lectin such as lectin RCA 120 from *Ricinus communis*. For the determination of sialo apolipoprotein B, the lectin SNA from *Sambucus nigra* can be used in a similar manner.

Further examples of the application of the method according to the invention are the detection of protein subpopulations with secondary modifications such as e.g. glycosylation, phosporylation, sulfation, presence of lipid residues such as farnesyl or myristoyl residues, the presence of prosthetic groups etc. or the detection of incompletely synthesized proteins. In this connection a specific antibody for the respective protein can be used as a first receptor and a lectin which is directed against a certain carbohydrate group or a further antibody which is for example specific for phosphotyrosine can be used as the second receptor.

A specific application of the method according to the invention is the detection of unglycosylated transferrin in the sera of alcoholics. In this case an antibody which recognizes a surface structure on transferrin which only occurs once is used as the first receptor. An antibody is used for the cross-linking, i.e. as the second receptor, which binds to a surface structure of the protein which is normally concealed by glycosylation. Normally glycosylated transferrin is not recognized by this second receptor since the glycosylation prevents the binding of the antibody.

A further subject matter of the present invention is a reagent kit for carrying out the method according to the invention, comprising (a) a first receptor which binds to an epitope which is only present once on the analyte to be determined and is immobilized on a particulate carrier material, (b) a second receptor which binds to a second epitope on the analyte and has at least two binding sites for the second epitope, the first epitope being different from the second epitope and (c) optionally suitable buffers.

It is intended to further elucidate the invention by the following examples.

EXAMPLE 1

Determination of Asialo and Sialo Apolipoprotein B 1.1 Reagents

For the preparation of the first receptor 10 mg carboxy-activated latex particles with a diameter of 282 nm were coupled to a monoclonal mouse anti-apolipoprotein B IgG (Boehringer Mannheim, Cat. No. 1484 273) by a standard method using EDC (N-ethyl-N'(3-dimethylaminopropyl) carbodiimide). The latex suspension was treated for 20 minutes at room temperature with 10 mM sodium periodate in order to oxidize the carbohydrate groups present on the antibody (cf. Marshall and Neuberger Structural analysis of the carbohydrate groups of glycoproteins: periodate oxidation methods, in: Gottschalk, A. ed., Glycoproteins 2nd ed., Amsterdam, Elsevier, 1972, Part A, pp. 331–341). The suspension was subsequently treated for 5 minutes with 1% ethanolamine in 50 mM Tris buffer pH 9 to inactivate the aldehyde groups that were formed during the oxidation. After the treatment the latex was centrifuged and taken up in storage buffer.

The lectins RCA 120 from *Ricinus communis* (Boehringer Mannheim, order no. 0223719) and SNA from *Sambucus nigra* (Vector, Cat. No. L-300) were used as second receptors.

Purified low density lipoprotein (LDL) was prepared by means of ultracentrifugation according to the method of Lindgren et al. (Lipid 10 (1975), 750–756).

1.2 Test Mixture and Measurement

Various amounts of sample (1.25–10 µl LDL, optionally sialidase treated) were added to 125 µl buffer, 25 µl latex (0.1%) or/and various amounts of the lectins RCA 120 or SNA. LDL (apo B) free serum or a serum with a known apo B content (apo B calibrated serum) were used as controls. The incubation was carried out in a photometer at 37° C. The measurement was carried out by monitoring the absorbance at 546 nm.

The results of this experiment are shown in the following table 1.

1.3 Evaluation of the Results

Table 1 shows that it is possible to determine the asialo subpopulation of apo B by the method according to the invention using the receptor combination antibody/lectin RCA 120. When the receptor combination antibody/lectin SNA is used it is possible to determine the sialo apolipoprotein B subpopulation.

In order to quantify the results obtained a calibration curve is established. For this an LDL preparation is completely desialylated by treatment with sialidase and a further LDL sample is completely sialylated by treatment with sialyl transferase and CMP-NANA. Apolipoprotein B preparations can be prepared from these two samples whose content of asialo apo B is known and which can be used to establish the calibration curve. The content of asialo or sialo apo B of a particular unknown preparation is read off from the calibration curve after measuring the agglutination rate.

TABLE 1

| | abs./min |
|---|---|
| Results first series latex beads | |
| buffer + latex | 0 |
| buffer + latex + 10 µl LDL | 0 |
| buffer + latex + RCA 120 (10 µg/ml) | 0 |
| buffer + latex + RCA 120 (10 µg/ml) + 1.25 µl LDL | 0.075 |
| buffer + latex + RCA 120 (10 µg/ml) + 2.5 µl LDL | 0.14 |
| buffer + latex + RCA 120 (10 µg/ml) + 5 µl LDL | 0.175 |
| buffer + latex + RCA 120 (10 µg/ml) + 10 µl LDL | 0.19 |
| buffer + latex + RCA 120 (10 µg/ml) + 10 µl apo B calib. serum | 0.09 |
| buffer + latex + RCA 120 (10 µg/ml) + 10 µl apo B free serum | 0 |
| Results second series latex beads | |
| buffer + latex | 0 |
| buffer + latex + 10 µl LDL | 0 |
| buffer + latex + RCA 120 (10 µg/ml) | 0 |
| buffer + latex + RCA 120 (5 µg/ml) + 10 µl LDL | 0.04 |
| buffer + latex + RCA 120 (10 µg/ml) + 10 µl LDL | 0.075 |
| buffer + latex + RCA 120 (10 µg/ml) + 10 µl LDL sialidase treat. | 0.1 |
| buffer + latex + RCA 120 (20 µg/ml) + 10 µl LDL | 0.09 |
| buffer + latex + RCA 120 (50 µg/ml) + 10 µl LDL | 0.19 |
| buffer + latex + RCA 120 (50 µg/ml) + 10 µl LDL sialidase treat. | 0.33 |
| Results third series latex beads | |
| buffer + latex + SNA (50 µg/ml) | 0 |
| buffer + latex + SNA + LDL free serum | 0 |
| buffer + latex + SNA + 10 µl LDL | 0.065 |
| buffer + latex + SNA + 10 µl LDL/sialidase treated | 0.01 |

What is claimed is:

1. A method for determining a first subpopulation of an analyte in a sample liquid which contains at least two subpopulations of the same analyte, comprising incubating the sample liquid with
(a) a first receptor which is immobilized on a particulate carrier, wherein the first receptor binds to a first epitope which is present on the members of each of the analyte subpopulations, wherein the first epitope is only present once per member, and
(b) a second receptor which binds to a second epitope which is present only on members of the first subpopulation, wherein the second receptor has at least two binding sites for the second epitope and wherein each of the at least two binding sites binds to a different member of the first analyte subpopulation to form a cross-linked structure, and determining the first analyte subpopulation by determining the cross-linked structure.

2. The method of claim 1, wherein the particulate carrier is selected from the group consisting of an inorganic particle, a latex particle, a liposome and a cell.

3. The method of claim 2, wherein the particulate carrier is a latex particle.

4. The method of claim 1, wherein at least one of the first receptor and the second receptor is selected from the group consisting of an antibody, an antibody fragment, a lectin, an aptamer and a membrane receptor.

5. The method of claim 1, wherein the first receptor is selected from the group consisting of a monoclonal antibody, or a fragment thereof, and a monospecific polyclonal antibody, or a fragment thereof.

6. The method of claim 1, wherein the first receptor is a lectin.

7. The method of claim 1, wherein the first receptor is an antibody, or a fragment thereof, and the second receptor is a lectin, or vice versa.

8. The method of claim 7, wherein the antibody or fragment thereof contains modified carbohydrate groups such that the antibody or fragment thereof is incapable of binding to the lectin.

9. The method of claim 1, wherein the determining step is carried out using a turbidimetric or a nephelometric assay.

10. The method of claim 1, wherein the determining step comprises determining the proportion of the first subpopulation of the analyte relative to the total amount of the analyte.

11. The method of claim 1, wherein the one of the at least two analyte subpopulations is a protein which differs from other subpopulations by the presence or absence of a secondary modification.

12. The method of claim 11, wherein the secondary modification is selected from the group consisting of a glycosylation, a specific pattern of glycosylation, a phosphorylation, a sulfation, the presence of a lipid residue and the presence of a prosthetic group.

13. The method of claim 1, wherein the method is performed without a step of separating bound and free receptors, or without a step of isolating any bound analyte.

14. A reagent kit for determining an analyte in a sample liquid, comprising a first receptor which binds to a first epitope which is present on the members of each of at least two subpopulations of the same analyte, wherein the first epitope is only present once per members, wherein the first receptor is immobilized on a particulate carrier, and a second receptor which binds to a second epitope which is present only on members of a first subpopulation, wherein the second receptor has at least two binding sites for the second epitope and wherein each of the at least two binding sites binds to a different member of the first analyte subpopulation to form a cross-linked structure.

15. The reagent kit of claim 14, further comprising a buffer.

* * * * *